United States Patent [19]

Cavazza

[11] 4,320,145

[45] Mar. 16, 1982

[54] PHARMACEUTICAL COMPOSITION FOR PARENTERAL NUTRITION COMPRISING L-CARNITINE OR ACYL L-CARNITINES

[76] Inventor: Claudio Cavazza, 47, Viale Shakespeare, 00144 Rome, Italy

[21] Appl. No.: 191,959

[22] Filed: Sep. 29, 1980

[30] Foreign Application Priority Data

Oct. 5, 1979 [IT] Italy ................... 50467 A/79

[51] Int. Cl.³ ................... A61K 31/205; A61K 31/195
[52] U.S. Cl. ................... 424/316; 424/319
[58] Field of Search ................... 424/316, 319

[56] References Cited

U.S. PATENT DOCUMENTS

| | | | |
|---|---|---|---|
| 3,830,931 | 8/1974 | De Felice | 424/319 |
| 3,968,241 | 7/1976 | De Felice | 424/319 |
| 4,194,006 | 3/1980 | Cavazza | 424/311 |

FOREIGN PATENT DOCUMENTS

| | | |
|---|---|---|
| 882936 | 4/1980 | Belgium . |
| 882937 | 4/1980 | Belgium . |

OTHER PUBLICATIONS

Strack et al., Hoppe Seyle Physiol. Chem. vol. 343, pp. 231–239 (1966).
Chem. Abstr. 78 (1973) entry 101978t.
Reynier et al. Revue Agressologie, 3(5), 711–719, (1962).
Madam et al., Drug Intelligence & Clin. Pharmacy, 10:684–696 (12/76).
Chem. Abstr. 82 (1975) entry 47745e.
Chem. Abstr. 85 (1976) entry 87551g.

*Primary Examiner*—Frank Cacciapaglia, Jr.
*Attorney, Agent, or Firm*—Bruce M. Collins

[57] ABSTRACT

A glucose solution for drip phleboclysis characterized by the inclusion therein of L-carnitine is disclosed. The presence of L-carnitine improves the muscle tissue absorption and utilization of glucose, thus preventing excessive insulin secretion. This permits the utilization of 10% glucose solutions, and also in excess of 10%, without any risk for the patient even in the case of long-term treatment.

10 Claims, 2 Drawing Figures

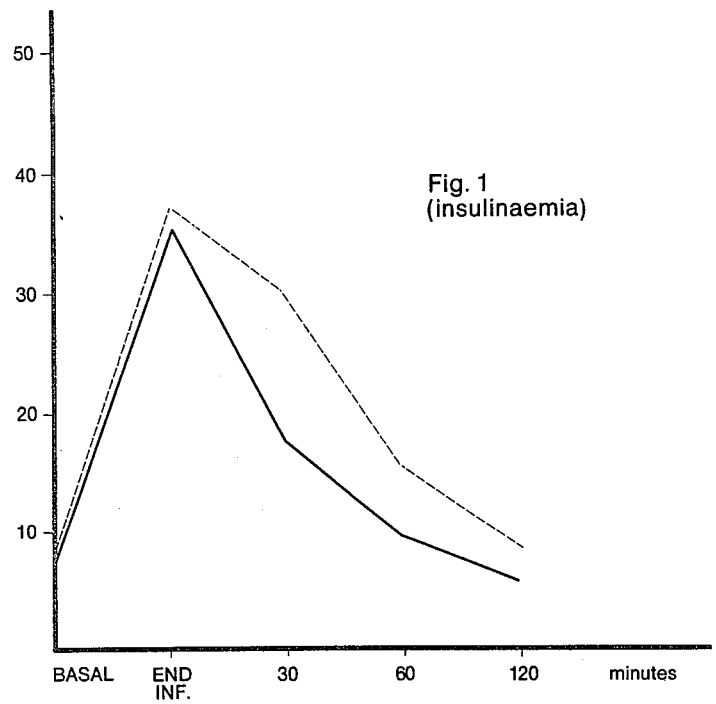
Fig. 1 (insulinaemia)
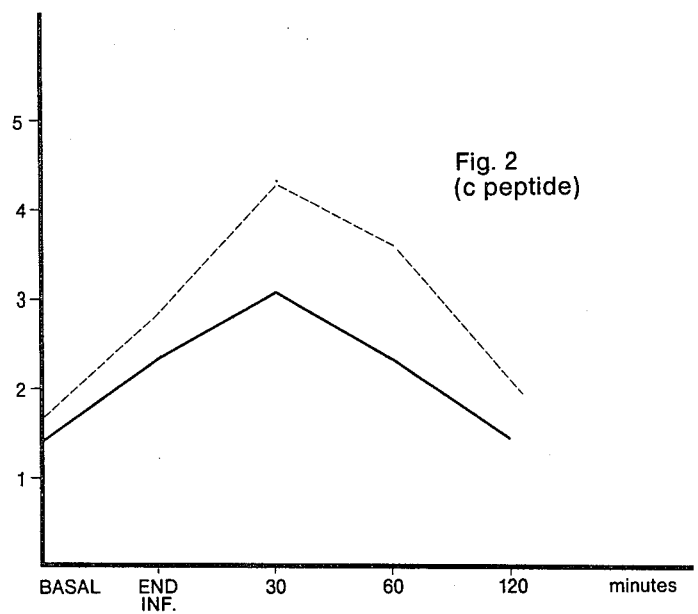
Fig. 2 (c peptide)
------------- Subject treated with 5% glucose solution
———— Subject treated with 5% glucose sol. +L-carnitine

PHARMACEUTICAL COMPOSITION FOR PARENTERAL NUTRITION COMPRISING L-CARNITINE OR ACYL L-CARNITINES

The present invention relates to a liquid pharmaceutical compositions for parenteral nutrition.

More specifically, the invention relates to a glucose solution for nutrition by drip phleboclysis of any type of patient who may require, over a more or less long period, to be fed via the parenteral route. Such a solution is, therefore, suitable for the nutrition of patients who need to receive nutrition via the parenteral route for a few days only, as in the case of patients who have been subjected to minor abdominal operations such as appendectomy or cholecystectomy, and for patients who cannot receive food via the enteral route for several weeks, as in the case of patients who have been subjected to extended resections of the intestinum tenue, esophageal perforations, etc.

During the postoperative period, there arises, among other problems, the problem of providing the patient with a supply of energy in a utilizable form. The patient, for more or less long periods, according to severity and extension of the surgical operation, is unable to absorb via the enteral route the saccharide, protein and lipid substrates which provide sources of utilizable energy.

The patient must, therefore, be fed via the parenteral route, generally by intravenous administration.

The supply of saccharides is indispensable as an energy source and for optimal protein synthesis, and it is known that approximately 200 grams per day are necessary in order to avoid the occurrence of gluconeogenesis from amino acids.

For a long time glucose supply has been given to the above-described patients by drip phleboclysis of glucose solutions: 5% glucose isotonic solutions and hypertonic solutions with up to 30% of glucose.

Both the isotonic and hypertonic solutions present serious and well-known inconveniences.

The isotonic solutions are absolutely insufficient for meeting the calorie requirements of an individual and for preventing the utilization of endogenous proteins. In fact, 500 cc of 5% glucose solutions contain 25 grams of glucose which produce 100 calories. At least 5 liters of such a glucose solution would have to be administered in order to obtain 1,000 calories corresponding to barely half of the metabolic requirements of a person at rest.

The infusion of solution with a high glucose content gives rise to even more serious inconveniences. There exists in fact the risk of provoking glycosuria. If this is particularly pronounced, unavoidably an osmotic effect will occur with secondary polyuria.

Another risk is represented by hyperglycaemia. It is known that the higher the glycaemia the more the $\beta$ cells of the islets of Langerhans are called upon to secrete insulin. Lutjens A., Verleur H. and Plooij M.: "Glucose and Insulin Levels in Loading with Different Carbohydrates". Clin. Chim. Acta, 62, (1975), 239. Rodger N. W., Squires B. P. and Du E. L.: "Changes in Plasma Insulin related to the type of Dietary Carbohydrates in Overweight Hyperlipidemic Male Patients". Canad. Med. Assoc. J., 105, (1971) 923.

It is also known that this stimulus represents a considerable risk of diabetes especially in subjects prone to this disease. It is in fact deemed that prolonged stressing action—mediated by hyperglycaemia—on the cells to secrete insulin, will determine irreversible depletion.

Other inconveniences are irritation of the vein into which the infusion is performed, also by slow infusions, even when the vein is of large diameter, and danger of septicaemia.

The parenteral administration of solutions of fructose, sorbitol and xylitol was proposed in the attempt to overcome the inconveniences posed by the use of glucose.

More than two decades of experimental studies and clinical observations have permitted to definitively conclude that the inconveniences and risks, sometimes even serious, associated with the parenteral administration of such substances in spite of the abovedescribed defects still give preference to glucose as the saccharide of choice.

For instance G. Van De Berghe and H. G. Hers in "Dangers of Intravenous Fructose and Sorbitol", Acta Paediatr. Belg. 31, 115–123 (1978) state that "the rapid metabolization of fructose as compared to glucose, instead of being an advantage, constitutes a potential danger in parenteral nutrition. As others do, we think that the use of fructose, invert sugar and sorbitol for this purpose should therefore strongly be disapproved". In fact, it is known that part of the fructose metabolized by the liver is converted into glucose with consequent hyperglycaemia.

If administered in remarkable amounts, especially to very underfed patients (or neonats), conversion into lactate will occur with consequent lactic acidosis, a rather serious event even if relatively frequent. Also some electrolytic imbalances, (particularly loss of Na and K) are more prominent in subjects treated by infusion of fructose versus those receiving comparable glucose solutions.

Xylitol, a sugar with 5 carbon atoms, metabolized by the pentose cycle and a source of toxic effects, is not superior to glucose with regard to calories.

It has also been proposed to add insulin to glucose solutions in order to facilitate the utilization of glucose and prevent proteolysis.

However, the addition of insulin poses a few problems. Above all, infusions of glucose-insulin increase the glucose concentration within the cells, with consequent hyperhydration of the cells themselves. Secondarily, if glucose infusion is not regular there may be a hypoglycaemic rebound linked to the high concentration of insulin in circulation as a response to the calories administered.

From what is mentioned above it is understood that none of the proposed saccharide solutions from the introduction into therapy of parenteral nutrition to the present day are adequately suitable for meeting the glucose demand of a patient who cannot be fed via the enteral route for quite long periods of time.

In order to complete the picture of the prior art which is relevant to the scope of the present invention it should be mentioned that it has also been proposed to add carnitine to a glucose solution in combination, however, with a lipid type substrate. In fact, M. Reynier, B. Broussolle, J. Drouet, B. Danoy and H. Laborit, in "Effets compares de perfusion de glucose seule et de glucose associe au 4-hydroxybutyrate de sodium avec on sans carnitine sur la survie du lapin soumis an jeune", Revue Agressologic, 3(5), 711–719, (1962) describe a study on the survival of rabbits subjected to water fasting, parenterally fed either with glucose solution alone, or with sodium 4-hydroxybutyrate-added glucose solution as the lipid substrate, or with lipid substrate+carnitine-added glucose solution.

The authors report that the rabbits fed with the glucose+lipid substrate+carnitine solution survive longer than those fed with glucose+lipid substrate solution and even longer than those fed with the glucose solution alone.

It is important to note that R. Reynier et al. emphasize the positive effect of carnitine when combined with glucose and 4-hydroxybutyrate on nitrogen metabolism, ignoring the possibility of utilizing the glucose solution with the sole addition of carnitine, that is without the lipid substrate; they omitted to investigate the effect of carnitine on insulin secretion provoked by glucose administration. In addition they used the racemic form of carnitine in their study and did not consider the possibility of being able to achieve different effects according to whether the racemic form or the two separated optical isomers are used. It is in fact known that carnitine presents an asymmetrical centre and therefore occur in the two D and L stereoisomer forms.

It has now been surprisingly found, and constitutes the basis of the present invention, that the presence in a glucose solution for parenteral nutrition of either L-carnitine or an acyl-L-carnitine wherein the acyl radical contains 2-6 carbon atoms, or the pharmaceutically acceptable salts, esters and amides thereof, determines a series of therapeutically advantageous effects, in no way inferable either by the prior art or in particular by the mentioned article by M. Reynier et al. In the pursuance of the present description L-carnitine alone will be referred to for the sake of simplicity, meaning however all the above compounds thereof.

It is essential to note that such therapeutically advantageous effects are determined by the fact that carnitine is L-carnitine, and not D-carnitine or the racemic form (D,L) utilized by the above authors.

It must be well understood that it has been discovered that the D-form is not just inactive compared to the L-form, that is it does not act as a simple "diluent" of the active L-form, but rather antagonizes the therapeutically advantageous effects of L-carnitine, at least partially nullyfying them.

More particularly it has been surprisingly found that the presence of L-carnitine in a glucose solution determines the following effects:

(a) Increased tissue utilization of glucose and, therefore, reduced glycaemia and decreased glucose level in the pheripheral blood.

(b) Disappearance of excessive insulin secretion which would occur in the absence of L-carnitine when administering an equal amount of glucose.

(c) Increased protein synthesis and glycogen-synthesis and therefore rapid replenishment of the body's energy reserves.

It is evident from the above effects (a) and (b) that it is possible, in the presence of L-carnitine, to utilize solutions with a high content (10%, 20%, 30%) of glucose without any risk to the patient, while it results from effect (c) that not only the amount is improved from the caloric point of view of what is administered to the patient but also the quality of the administration.

Therefore, the object of the present invention is constituted by a pharmaceutical composition administerable parenterally for the nutrition of patients who cannot be fed via the enteral route comprising: a nutritionally effective amount of glucose; an amount of either L-carnitine or acyl-L-carnitine wherein the acyl group has 2-6 carbon atoms, or a pharmaceutically acceptable salt, ester or amide thereof, sufficient to increase glucose utilization, and to simultaneously avoid excessive insulin secretion in said patients; and a pharmaceutically acceptable liquid excipient.

A preferred embodiment of the composition according to the invention comprises:
glucose: 50–300 g/l
L-carnitine, acyl-L-carnitine wherein the acyl radical has 2-6 carbon atoms or the pharmaceutically acceptable salt, ester or amide thereof: 1–10 g/l
distilled water: balance to 1 liter Among the acyl groups, acetyl, propionyl, pyruvyl, butyryl, hydroxybutyryl and hesanoyl are preferred. Acetyl and pyruvyl are particularly preferred.

As already mentioned the carnitine content is solely L-carnitine.

The term "solely L-carnitine" means, for the purpose of the present invention, not only that the component of the composition constituted by carnitine is substantially pure L-carnitine, that is disregarding possible impurities or traces of D-carnitine, but also that carnitine can prevalently be L-carnitine, that is clearly exceeding the amount of D-carnitine, for instance by an L:D ratio of 95:5.

According to another composition embodiment of the invention, the composition will comprise an amino-acid complex. The amount of the amino-acid complex will generally be comprised between 25 g/l and 70 g/l.

Amino-acid compositions and protein hydrolysates as source of amino-acids, suitable for parenteral nutrition are well known to those skilled in this art. Commercially available amino-acid-containing compositions for intravenous hyperalimentation are disclosed, for instance, in "Total parenteral nutrition" by Parshotam L. Madam, Devendra K. Madam and Joseph F. Palumbo, Drug Intelligence and Clinical Pharmacy, vol. 10 Dec. 76, 684–696, the disclosures of this article being incorporated herein by reference.

Non limiting examples of suitable amino-acid-containing compositions in accordance with the present invention are the following:

| Composition A | |
| --- | --- |
| glucose | 50–300 g/l |
| L-carnitine | 1–10 g/l |
| Leucine | 8–10 g/l |
| Valine | 6–8 g/l |
| Lysine | 6–8 g/l |
| Isoleucine | 5–6 g/l |
| Phenylalanine | 4–5 g/l |
| Threonine | 3–4.5 g/l |
| Methionine | 2.5–3.5 g/l |
| Histidine | 2.5–3.5 g/l |
| Tryptophan | 0.5–1.0 g/l |
| Distilled water | balance to 1 l. |

| Composition B | |
| --- | --- |
| glucose | 50–300 g/l |
| L-carnitine | 1–10 g/l |
| L-leucine | 6.5–8 g/l |
| L-valine | 1.5–2 g/l |
| L-lysine | 4–5 g/l |
| L-isoleucine | 2.5–3 g/l |
| L-phenylalanine | 1–1.5 g/l |
| L-threonine | 2.5–3 g/l |
| L-methionine | 1–1.5 g/l |
| L-arginine | 2.5–3.5 g/l |
| L-histidine | 1–1.5 g/l |
| L-tryptophan | 0.5–1.0 g/l |
| L-tyrosine | 1–1.5 g/l |
| L-glutamic acid | 0.3–0.5 g/l |

-continued

| | |
|---|---|
| L-aspartic acid | 0.3–0.5 g/l |
| L-cysteine | 0.3–0.5 g/l |
| glycine | 2–2.5 g/l |

Experimental tests

The effect of L-carnitine on glucose uptake in rat diaphragm preparations was studied (see tables 1 and 2).

TABLE 1

Effect of L-carnitine on glucose Uptake in Rat Diaphragm Preparations

| | |
|---|---|
| Animals: | Wistar rats ♀, weighing 180–200 g, fed ad libitum |
| Method: | Diaphragm preparation according to P.J. Randle and G. H. Smith's technique (Biochem. J., 70, 490, 1958) The hemidiaphragms are incubated for 60 minutes at 37° C. in 3 ml of Krebs-Ringer-Bicarbonate medium pH 7.4, in the presence of 8.3 mM of glucose. |
| Calculations: | Glucose Uptake = Initial glucose concentration in the medium - final glucose concentration in the medium |

| Addition to the Incubation medium | | Glucose Uptake mg/g wet wt./hr | | Difference | Significance of Difference |
|---|---|---|---|---|---|
| Buffer | | $3.15 \pm 0.20^a$ | (12) | | |
| Insulin | (0.1 U/ml) | $5.26 \pm 0.25$ | (12) | $2.11 \pm 0.18$ | $p < 0.001$ |
| Buffer | | $3.45 \pm 0.25$ | (9) | | |
| D, L-carnitine | ($10^{-3}$M) | $3.64 \pm 0.29$ | (9) | $0.19 \pm 0.29$ | n.s. |
| Buffer | | $3.13 \pm 0.21$ | (8) | | |
| L-carnitine | ($10^{-3}$M) | $4.04 \pm 0.19$ | (8) | $0.91 \pm 0.28$ | $p < 0.01$ |
| Buffer | | $3.12 \pm 0.13$ | (9) | | |
| D-carnitine | ($10^{-3}$M) | $3.65 \pm 0.14$ | (9) | $0.53 \pm 0.12$ | $p < 0.01$ |

$a$ = Mean Value ± standard error
In parentheses, number of hemidiaphragms

TABLE 2

Effect of L-Carnitine on glucose Uptake in Rat Diaphragm Preparations

| Addition to the Incubation medium | | Glucose Uptake mg/g wet wt./hr | Difference | Significance of Difference |
|---|---|---|---|---|
| Insulin | (0.1 U/ml) | $5.72 \pm 0.34^a$ (6) | | |
| Insulin | (0.1 U/ml) | | | |
| D, L-carnitine | ($10^{-3}$M) | $5.19 \pm 0.50$ (6) | $-0.53 \pm 0.48^a$ | n.s. |
| Insulin | (0.1 U/ml) | $5.78 \pm 0.32$ (8) | | |
| Insulin | (0.1 U/ml) | | | |
| L-carnitine | ($10^{-3}$M) | $6.33 \pm 0.30$ (8) | $+0.55 \pm 0.15$ | $p < 0.01$ |
| Insulin | (0.1 U/ml) | $5.76 \pm 0.26$ (6) | | |
| Insulin | (0.1 U/ml) | | | |
| D-carnitine | ($10^{-3}$M) | $5.19 \pm 0.14$ (6) | $-0.57 \pm 0.27$ | n.s. |

$a$ = Mean Value ± standard error
In parentheses, number of hemidiaphragms

The present invention will also comprise a method for nourishing patients who need to receive nutrition via the parenteral route. Such a method comprises administering parenterally, in particular intravenously, a nutritionally effective amount of glucose, and in combination with glucose, an amount of L-carnitine, acyl-L-carnitine wherein the acyl group has 2-6 carbon atoms, or a pharmaceutically acceptable salt, ester or amide thereof.

The effectiveness of L-carnitine in the parenteral nutrition with glucose-containing solutions has been proved by several experimental studies and clinical cases, some of which are hereinbelow illustrated.

CLINICAL STUDIES

A group of 10 male and female patients between 39 and 74 years of age, which had been previously subjected to surgical operations, were admitted to the trial.

These patients showed no signs of concomitant diseases during the post-surgical periods.

The patients were first put on 120-min drip of 5% glucose solution and then on 120-min drip of 5% glucose solution containing L-carnitine (40 mg/kg body weight). Between the first and the second infusion, a 18-hour interval elapsed.

Immediately prior to initiating each infusion, at the end of infusion and at +30 min, +60 min. and +120 min., blood samples were drawn for determining blood glucose, insulinaemia and C peptide. C peptide was determined by the Heding's method. The test results are summarized in Tables 3, 4 and in FIGS. 1, 2.

TABLE 3

Glycaemia and insulin values after administration of a 5% glucose solution and glucose solution + L-carnitine 40 mg/kg.
Infusion time: 2 hr.
Basal values at the end of infusion and at 30 minutes, 60 minutes and 120 minutes.

| BASAL | | | | END OF INFUSION | | | |
|---|---|---|---|---|---|---|---|
| glucose solution 5% | | glucose solution 5% + L-carnitine 40 mg/kg | | glucose solution 5% | | glucose solution 5% + L-carnitine 40 mg/kg | |
| glycemia | Insulin | glycemia | Insulin | glycemia | Insulin | glycemia | Insulin |
| 91 | 7.8 | 99 | 10 | 162 | 52.8 | 193 | 26.2 |
| 95 | 9 | 103 | 8.7 | 184 | 50.8 | 242 | 61.7 |
| 86 | 6.4 | 94 | 5 | 144 | 17.3 | 190 | 24.4 |
| 88 | 6.6 | 79 | 3.5 | 166 | 21 | 162 | 17.8 |
| 82 | 2.5 | 87 | 4 | 152 | 28.5 | 194 | 23 |
| 102 | 6 | 84 | 4.5 | 177 | 10.5 | 165 | 29 |
| 103 | 2.5 | 89 | 2 | 135 | 10.6 | 228 | 29 |
| 78 | 6.5 | 93 | 6.1 | 142 | 27.2 | 144 | 17.4 |
| 93 | 8.8 | 90 | 8.7 | 177 | 39.2 | 205 | 8.2 |
| 87 | 15.6 | 88 | 15.8 | 127 | 106.2 | 234 | 88.6 |
| M 90.5 | 7.17 | 91.6 | 6.8 | 156.6 | 36.4 | 195.7 | 34.5 |
| SD ± 8.0 | ±3.7 | ±7.4 | ±4 | ±19.5 | ±28.7 | ±32.5 | ±22.7 |
| Var ± 50.2 | ±12.3 | ±50 | ±14.9 | ±343.6 | ±744.1 | ±953.4 | ±464.1 |

| +30 minutes | | | | +60 minutes | | | | +120 minutes | | | |
|---|---|---|---|---|---|---|---|---|---|---|---|
| glucose solution 5% | | glucose solution 5% +L-carnitine 40 mg/kg | | glucose solution 5% | | glucose solution 5% +L-carnitine 40 mg/kg | | glucose solution 5% | | glucose solut. 5% +L-carnitine 40 mg/kg | |
| glycemia | Insulin | glycemia | Insulin | glycemia | Insulin | glycemia | Insulin | glycemia | Insulin | glycemia | Insulin |
| 94 | 28.3 | 115 | 21.5 | 96 | 24 | 82 | 11.4 | 95 | 13 | 85 | 2.4 |
| 127 | 22.7 | 192 | 39 | 98 | 13.2 | 136 | 20.4 | 84 | 9.8 | 99 | 10.6 |
| 88 | 6 | 85 | 10.4 | 82 | 5 | 74 | 6.5 | 89 | 5 | 66 | 3 |
| 106 | 9.7 | 99 | 8.4 | 79 | 6.7 | 84 | 3.5 | 84 | 3 | 78 | 2 |
| 117 | 20.5 | 143 | 17.4 | 97 | 17.5 | 108 | 13.5 | 86 | 10.2 | 81 | 7.4 |
| 111 | 42 | 97 | 11 | 89 | 20.6 | 93 | 2 | 70 | 8.2 | 85 | 2.5 |
| 80 | 34.2 | 115 | 14.6 | 59 | 18.6 | 87 | 5 | 68 | 8.4 | 77 | 3 |
| 97 | 25.1 | 108 | 16.6 | 78 | 12.2 | 77 | 3.4 | 77 | 8.6 | 64 | 2 |
| 105 | 26.2 | 108 | 14.5 | 77 | 10.3 | 78 | 6.2 | 69 | 8.4 | 50 | 4.2 |
| 85 | 88.2 | 87 | 25.3 | 75 | 32 | 72 | 12.5 | 88 | 15 | 76 | 6 |
| 101 | 30.2 | 114.9 | 178 | 83 | 16 | 89.1 | 8.4 | 81 | 8.96 | 76.1 | 4.3 |
| ±14.9 | ±22.9 | ±31.7 | ±9 | ±12.2 | ±8.2 | ±19.5 | ±5.8 | ±9.4 | ±3.4 | ±13.5 | ±2.8 |
| ±200.4 | ±472 | ±907.4 | ±73.1 | ±134.4 | ±61.2 | ±344.2 | ±30.5 | ±80.5 | ±10.7 | ±164 | ±7.3 |

10 cases Insulin
30 minutes Student's t: 1,679: < 0,20
60 minutes Student's t: 2,509: < 0,025
120 minutes Student's t: 3,473: < 0,005

TABLE 4

| C PEPTIDE after administration of a 5% glucose solution | | | | | |
|---|---|---|---|---|---|
| | Basal | End of infusion | 30 min. | 60 min. | 120 min. |
| M. | 1,55 | 2,77 | 4,12 | 3,42 | 2,3 |
| S.D. | 0,51 | 2,0 | 2,3 | 2,36 | 1,46 |
| VAR. | 0,238 | 3,63 | 4,76 | 5,02 | 1,92 |

| C PEPTIDE after administration of a 5% glucose solution + L-carnitina (40 mg/kg) | | | | | |
|---|---|---|---|---|---|
| M. | 1,4 | 2,15 | 2,86 | 2,16 | 1,47 |
| S.D. | 0,41 | 1,46 | 1,76 | 1,74 | 0,79 |
| VAR. | 0,158 | 1,93 | 2,81 | 2,74 | 0,568 |

30 minutes student's t = 1,448 0,2 Δ% - 30,5
60 minutes student's t = 1,4302 0,2    - 36,8
120 minutes student's t = 1,6639 0,2    - 36,08

What is claimed is:

1. A parenterally administrable pharmaceutical composition useful for nourishing patients who cannot be fed via the enteral route, consisting essentially a nutritionally effective amount of glucose, an amount of L-carnitine or acyl-L-carnitine wherein the acyl group has 2-6 carbon atoms, or a pharmaceutically acceptable salt, ester or amide thereof, sufficient to enhance glucose utilization whilst avoiding excessive insulin secretion in said patients, said L-carnitine or acyl-L-carnitine being solely the L-isomer or a mixture of the L- and D-isomers in an L:D ratio of at least 95:5; and a pharmaceutically acceptable liquid excipient therefor.

2. The pharmaceutical composition of claim 1, administrable by drip phleboclysis, consisting essentially:
   glucose: 50-300 g/l
   L-carnitine or acyl-L-carnitine wherein the acyl group has 2-6 carbon atoms, or a pharmaceutically acceptable salt, ester or amide thereof: 1-10 g/l
   distilled water: balance to 1 liter.

3. The pharmaceutical composition of claim 2, wherein said acyl group is selected from the group consisting of acetyl, pyruvyl, propionyl, butyryl, hydroxybutyryl and hexanoyl.

4. The pharmaceutical composition according to claim 1, which also comprises a nutritionally effective amount of a mixture of amino-acids.

5. The pharmaceutical composition of claim 4, wherein said amount of amino acid mixture is comprised between 25 g/l and 75 g/l.

6. The pharmaceutical composition of claim 5 comprising:
   glucose: 50-300 g/l
   L-carnitine: 1-10 g/l
   Leucine: 8-10 g/l
   Valine: 6-8 g/l
   Lysine: 6-8 g/l
   Isoleucine: 5-6 g/l
   Phenylalanine: 4-5 g/l
   Threonine: 3-4.5 g/l
   Methionine: 2.5-3.5 g/l
   Histidine: 2.5-3.5 g/l
   Tryptophan: 0.5-1.0 g/l
   Distilled water: balance to 1 l.

7. The pharmaceutical composition of claim 5 comprising:
   glucose: 50-300 g/l
   L-carnitine: 1-10 g/l L-leucine: 6.5–8 g/l
L-valine: 1.5–2 g/l
L-lysine: 4–5 g/l
L-isoleucine: 2.5–3 g/l
L-phenylalanine: 1–1.5 g/l
L-threonine: 2.5–3 g/l
L-methionine: 1–1.5 g/l
L-arginine: 2.5–3.5 g/l
L-histidine: 1–1.5 g/l
L-tryptophan: 0.5–1.0 g/l
L-tyrosine: 1–1.5 g/l
L-glutamic acid: 0.3–0.5 g/l
L-aspartic acid: 0.3–0.5 g/l
L-cysteine: 0.3–0.5 g/l
glycine: 2–2.5 g/l.

8. A method of nourishing patients in need of parenteral nutrition which comprises administering by the parenteral route to said patients a nutritionally effective amount of glucose and in combination therewith an amount of L-carnitine or acyl-L-carnitine wherein the acyl group has 2–6 carbon atoms, or a pharmaceutically acceptable salt, ester or amide thereof, said L-carnitine or acyl-L-carnitine being solely the L-isomer or a mixture of the L- and D-isomers in an L:D ratio of at least 95:5.

9. The method of claim 8, which comprises administering by drip phleboclysis the following composition:
glucose: 50–300 g/l
L-carnitine or acyl-L-carnitine wherein the acyl group has 2–6 carbon atoms, or a pharmaceutically acceptable salt, ester or amide thereof: 1–10 g/l
distilled water: balance to 1 liter.

10. The pharmaceutical composition according to claim 1, consisting essentially of said glucose, a nutritionally effective amount of a mixture of amino acids, said L-carnitine or acyl-L-carnitine or pharmaceutically acceptable salt, ester or amide thereof and said liquid excipient.

* * * * *